(12) United States Patent
Stubenrauch et al.

(10) Patent No.: US 8,227,195 B2
(45) Date of Patent: Jul. 24, 2012

(54) DISTINGUISHING ASSAY

(75) Inventors: Kay-Gunnar Stubenrauch, Penzberg (DE); Markus Zadak, Sindelsdorf (DE)

(73) Assignee: Hoffman-La Roche Inc., Nutley, NJ (US)

( * ) Notice: Subject to any disclaimer, the term of this patent is extended or adjusted under 35 U.S.C. 154(b) by 184 days.

(21) Appl. No.: 12/745,565

(22) PCT Filed: Dec. 12, 2008

(86) PCT No.: PCT/EP2008/010575
§ 371 (c)(1), (2), (4) Date: Jun. 1, 2010

(87) PCT Pub. No.: WO2009/077127
PCT Pub. Date: Jun. 25, 2009

(65) Prior Publication Data
US 2010/0304400 A1    Dec. 2, 2010

(30) Foreign Application Priority Data

Dec. 15, 2007 (EP) .................................. 07024353
Feb. 11, 2008 (EP) .................................. 08002450

(51) Int. Cl.
*G01N 33/53* (2006.01)
(52) U.S. Cl. .......................... 435/7.1; 435/7.2; 436/518
(58) Field of Classification Search .................. None
See application file for complete search history.

(56) References Cited

U.S. PATENT DOCUMENTS

| 5,202,238 A | 4/1993 | Fell, Jr. et al. |
| 5,204,244 A | 4/1993 | Fell, Jr. et al. |
| 5,219,730 A | 6/1993 | Potocnjak et al. |

FOREIGN PATENT DOCUMENTS

| EP | 0139389 | 2/1985 |
| EP | 0170302 | 5/1986 |
| EP | 0580979 | 2/1994 |
| WO | 87/02778 | 5/1987 |
| WO | 90/05301 | 5/1990 |
| WO | 90/06515 | 6/1990 |
| WO | 90/11511 | 10/1990 |
| WO | 92/14138 | 8/1992 |
| WO | 98/33523 | 8/1998 |
| WO | 98/52976 | 11/1998 |
| WO | 00/34317 | 6/2000 |
| WO | 03/080675 | 10/2003 |
| WO | 2005/045058 | 5/2005 |
| WO | 2006/072564 | 7/2006 |
| WO | 2006/107962 | 10/2006 |
| WO | 2007/101661 | 9/2007 |

OTHER PUBLICATIONS (Translation of Japanese Off Act for Corr App 2010537321 Nov. 2, 2011).

Lofgren, J. et al "Comparing ELISA and sruface plasmon resonance for assessing clinical immunogenicity of panitumuab" Jour. of Immunology 178:11 (2007) 7467-7472 XP002473717.
Bourdage et al, "Effect of double antigen bridging immunoassay format on antigen coating concentration dependence and implications for desiging immunogenicity assays for monoclonal antibodies" Jour. of Pharmaceutical and Biomedical Analysis, 39:3-4, (2005) 685-690 XP005039077.
Mire-Sluis A R et al "Recommendations for the design and optimization of immunoassays used in the detection of host antibodies against biotechnology products" Jour. of Immujnological Methods, 289:1-2 (2004) 1-16 XP004520874.
Baert F et al, "Influence of immunogenicty on the long-term efficacy of infliximab in Crohn's Disease" New England Journal of Medicine 348:7 (2003) 601-608 XP009037271.
Gross et al, "Detection of anti-EPO antibodies in human sera by a bridging ELISA is much more sensitive when coating biotinylated rhEPO to streptavidin rather than using direct coating of rhEPO" Jour. of Immunolgoical Methdos 313:1-2 (2006) 176-182 XP005542644.
Aikawa, M. et al, Cytokine 13 (2001) 75-84.
Aslam M. and Dent A, Bioconjugation Macmillan Ref. Ltd. (1999) 50-100.
Bird, R.E. et al, Science 242 423-426, Year 1988.
Butler, J.E., Methods 22 (2000) 4-23.
Graber,P. et al Eur.J. Immunol. 28 (1998) 4286-4298.
Hage, D.S. Anal. Chem. 71 (1999) 294R-304R.
Hoesel, W. et al, J. Immunol. Methods 294:101-110 (2004).
Hunkapiller, T. Nature 323 (1986) 15-16.
Huston,J.S. et al, PNAS 85 (1988) 5879-5883.
Huston, JS et al, Methods in Enzymol. 203 (1991) 46-88.
Lonberg, N. Nat. Biotechnol. 23 (2005) 1117-1125.
Lu, B. et al, Analyst 121 (1996) 29R-32R.
Martin,C.R. et al, Analytical Chemistry News & Features (1998) 322A-327A.
Morrison, S.L. et al, Proc. Natl. Acad. Sci. 81 (1984) 6851-6855.
Neuberger, M.S. et al, Nature, 314 (1985) 268-270.
Pan, Y et al, FASEB J. 9 (1995) 43-49.
Poudrier, J. et al, Eur. J. Immunol,. 30 (2000) 3157-3164.
Poudrier, J. et al, J. Immunol. 163 (1999) 1153-1161.
Reichmann, L. et al, Nature 332 (1988) 323-327.
Wadhwa, M. et al, J. Immunol. Methods 278 (2003) 1-17.
Wilchek, M. and Bayer, E.A. Methods Enzymol. 184 (1990) 467-469.

*Primary Examiner* — Jacob Cheu
(74) *Attorney, Agent, or Firm* — George W. Johnston; Dennis P. Tramaloni; Samuel H. Megerditchian

(57) ABSTRACT

The current invention comprises a method for determining of an antibody against a drug antibody in a sample using an immunoassay comprising a capture drug antibody and a tracer drug antibody, wherein the method comprises providing i) a capture drug antibody, which is the drug antibody conjugated to a solid phase, ii) a tracer drug antibody, which is the drug antibody conjugated to a detectable label, contacting the capture drug antibody separately with i) the sample, ii) the sample, to which the drug antibody in monomeric form has been added, iii) the sample, to which the drug antibody in oligomeric form has been added, and determining an antibody against the drug antibody in the sample by a positive immunoassay in i) and a negative immunoassay in ii) and iii).

4 Claims, 1 Drawing Sheet

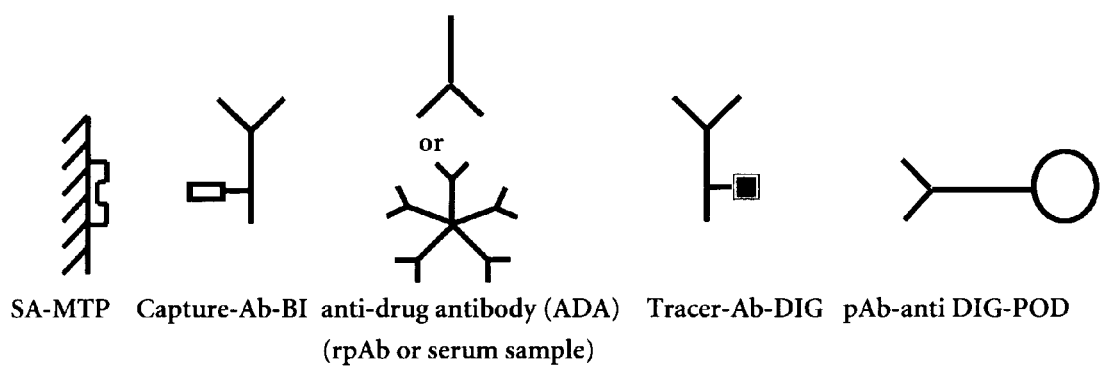

DISTINGUISHING ASSAY

This application is the National Stage of International Application No. PCT/EP2008/010575, filed Dec. 12, 2008, which claims the benefit of EP 08002450.8 filed Feb. 11, 2008 and EP 07024353.0 filed Dec. 15, 2007, each of which is hereby incorporated by reference in its entirety.

The invention comprises a method for distinguishing the presence of specific and not-specific anti-drug antibodies in a sample, as well as kits for the use of such a method.

BACKGROUND OF THE INVENTION

Standard solid-phase immunoassays with monoclonal antibodies involve the formation of a complex between antibody adsorbed on a solid phase (capture antibody), antigen, and antibody to another epitope of the antigen conjugated to a detectable label, e.g. an enzyme (tracer antibody). Thus, a sandwich is formed: solid phase-capture antibody-antigen-tracer antibody. In the reaction catalyzed by the sandwich, the activity of the antibody-conjugated enzyme is proportional to the antigen concentration in the incubation medium. The standard sandwich method is also called double antigen bridging immunoassay because capture and tracer antibodies bind to different epitopes of the same antigen. Hoesel, W., et al., J. Immunol. Methods 294 (2004) 101-110, report an anti-EPO double antigen bridging assay whereby a mixture of immobilized rhEPO coupled to amino groups and to carbohydrate groups was used. Immunoassays such as the double antigen bridging ELISA are common assay types in the investigation of an immunogenic answer of a patient to an antibody drug. Mire-Sluis, A. R., et al., J. Immunol. Methods 289 (2004) 1-16, summarize the recommendations for the design and optimization of immunoassays using detection of host antibodies against biotechnology products. According to Mire-Sluis et al. the well-known anti-drug antibody assay formats show considerable disadvantages. Anti-drug antibody assays are mentioned, for example, in WO 2005/045058 and WO 90/006515. Anti-idiotypic antibody assays are mentioned, for example, in U.S. Pat. No. 5,219,730, WO 87/002778, EP 0 139 389, and EP 0 170 302. Wadhwa, M., et al., J. Immunol. Methods 278 (2003) 1-17, report strategies for the detection, measurement and characterization of unwanted antibodies induced by therapeutic biologicals. The principles of different immunoassays are described, for example, by Hage, D. S., Anal. Chem. 71 (1999) 294R-304R. Lu, B., et al., Analyst. 121 (1996) 29R-32R, report the orientated immobilization of antibodies for the use in immunoassays. Avidin-biotin-mediated immunoassays are reported, for example, by Wilchek, M., and Bayer, E. A., Methods Enzymol. 184 (1990) 467-469. A comparison of ELISA and surface plasmon resonance was reported by Lofgren, J. A., et al., J. Immunol. 178 (2007) 7467-7472.

SUMMARY OF THE INVENTION

The first aspect of the current invention is a method for determining an antibody against a drug antibody (anti-drug antibody, ADA) in a sample using an immunoassay comprising a capture drug antibody and a tracer drug antibody, wherein said method comprises the following steps:
a) providing
   a-i) said capture drug antibody, which is said drug antibody conjugated to a solid phase,
   a-ii) said tracer drug antibody, which is said drug antibody conjugated to a detectable label,
b) contacting said capture drug antibody separately with
   b-i) said sample,
   b-ii) said sample, to which said drug antibody in monomeric form has been added prior to the immunoassay,
   b-iii) said sample, to which said drug antibody in oligomeric form has been added prior to the immunoassay,
c) determining an antibody against said drug antibody in said sample by a positive immunoassay in b-i) and a negative immunoassay in b-ii) and b-iii).

Another aspect of the current invention is a method for determining whether an antibody present in a sample is a specific anti-drug antibody or a not-specific anti-drug antibody using a double antigen bridging immunoassay comprising a capture drug antibody and a tracer drug antibody, wherein said method comprises the following steps:
a) providing
   a-i) said capture drug antibody, which is said drug antibody conjugated to a solid phase,
   a-ii) said tracer drug antibody, which is said drug antibody conjugated to a detectable label,
b) contacting said capture drug antibody separately with
   b-i) said sample,
   b-ii) said sample, to which said drug antibody in monomeric form has been added,
   b-iii) said sample, to which said drug antibody in oligomeric form has been added,
   b-iv) said sample, to which human immunoglobulin G in monomeric form has been added,
   b-v) said sample, to which human immunoglobulin G in oligomeric form has been added,
c) determining an antibody present in said sample to be a specific anti-drug antibody by a positive immunoassay in b-i) and b-iv) and b-v) and a negative immunoassay in b-ii) and b-iii), or
determining an antibody present in said sample to be a not-specific anti-drug antibody by a positive immunoassay in b-i) and b-ii) and b-iv) and a negative immunoassay in b-iii) and b-v).

The third aspect of the current invention is a method for distinguishing in a sample an anti-drug antibody to a humanized anti-inflammatory drug antibody from an anti-human IgG antibody with an immunoassay, wherein the method comprises the following steps:
a) providing
   a-i) a capture drug antibody, which is said drug antibody conjugated to a solid phase,
   a-ii) a tracer drug antibody, which is said drug antibody conjugated to a detectable label,
b) contacting said capture drug antibody separately with
   b-i) said sample,
   b-ii) said sample, to which said drug antibody in monomeric form has been added,
   b-iii) said sample, to which said drug antibody in oligomeric form has been added,
   b-iv) said sample, to which human immunoglobulin G in monomeric form has been added,
   b-v) said sample, to which human immunoglobulin G in oligomeric form has been added,
c) determining an anti-drug antibody to a humanized anti-inflammatory drug antibody by a positive immunoassay in b-i) and b-iv) and b-v) and a negative immunoassay in b-ii) and b-iii), or
determining an antibody present in said sample to be an anti-human IgG antibody by a positive immunoassay in b-i) and b-ii) and b-iv) and a negative immunoassay in b-iii) and b-v).

Still a further aspect of the current invention is a method for determining whether an anti-drug antibody in a sample is of monomeric or oligomeric form with an immunoassay, wherein the method comprises the following steps:
a) providing
  a-i) a capture drug antibody, which is said drug antibody conjugated to a solid phase,
  a-ii) a tracer drug antibody, which is said drug antibody conjugated to a detectable label,
b) contacting said capture drug antibody separately with
  b-i) said sample,
  b-ii) said sample, to which said drug antibody in monomeric form has been added,
  b-iii) said sample, to which said drug antibody in oligomeric form has been added,
  b-iv) said sample, to which human immunoglobulin G in monomeric form has been added,
  b-v) said sample, to which human immunoglobulin G in oligomeric form has been added,
c) determining the anti-drug antibody in the sample to be of monomeric form by a positive immunoassay in b-i) and
  α) a negative immunoassay in b-ii) and b-iii), or
  β) a negative immunoassay in b-ii), b-iii), b-iv), and b-v), or
determining an anti-drug antibody in the sample to be of oligomeric form by a positive immunoassay in b-i) and
  α) a negative immunoassay in b-iii), or
  β) a negative immunoassay in b-iii) and b-v),
whereby all other not listed immunoassay are positive.

Another aspect of the current invention is a method for determining the presence of oligomeric anti-drug antibodies in a sample with an immunoassay, wherein the method comprises the following steps:
a) providing
  a-i) a capture drug antibody, which is said drug antibody conjugated to a solid phase,
  a-ii) a tracer drug antibody, which is said drug antibody conjugated to a detectable label,
b) contacting said capture drug antibody separately with
  b-i) said sample,
  b-ii) said sample, to which said drug antibody in monomeric form has been added,
  b-iii) said sample, to which said drug antibody in oligomeric form has been added,
  b-iv) said sample, to which human immunoglobulin G in monomeric form has been added,
  b-v) said sample, to which human immunoglobulin G in oligomeric form has been added,
c) determining the anti-drug antibody in a sample to be of oligomeric form by a positive immunoassay in b-i) and b-iii) and b-v) and a negative immunoassay in b-ii) and b-iv).

A further aspect of the current invention is a method for determining the class of an anti-drug antibody determined in a sample with an immunoassay, wherein the method comprises the following steps:
a) providing
  a-i) a capture drug antibody, which is said drug antibody conjugated to a solid phase,
  a-ii) a tracer drug antibody, which is said drug antibody conjugated to a detectable label,
b) contacting said capture drug antibody separately with
  b-i) said sample,
  b-ii) said sample, to which said drug antibody in monomeric form has been added,
  b-iii) said sample, to which said drug antibody in oligomeric form has been added,
  b-iv) said sample, to which human immunoglobulin G in monomeric form has been added,
  b-v) said sample, to which human immunoglobulin G in oligomeric form has been added,
c) determining the class of an anti-drug antibody to be a monomeric and drug antibody specific anti-drug antibody by a positive immunoassay in b-i) and b-iv) and b-v) and a negative immunoassay in b-ii) and b-iii), or
determining the class of an anti-drug antibody to be an oligomeric and drug antibody specific anti-drug antibody by a positive immunoassay in b-i) and b-ii) and b-iv) and b-v) and a negative immunoassay in b-iii), or
determining the class of an anti-drug antibody to be a oligomeric and not drug antibody specific antibody by a positive immunoassay in b-i) and b-ii) and b-iv) and a negative immunoassay in b-iii) and b-v), or
determining the class of an anti-drug antibody to be a monomeric and not drug antibody specific antibody by a positive immunoassay in b-i) and a negative immunoassay in b-ii) and b-iii) and b-iv) and b-v).

In one embodiment the class of an anti-drug antibody is determined according to the following table:

|   | drug antibody specific, monomeric response | drug antibody specific, oligomeric response | drug antibody unspecific, oligomeric response | drug antibody unspecific, monomeric response | drug antibody unspecific response |
|---|---|---|---|---|---|
| Un-spiked sample b-i) | + | + | + | + | + |
| b-ii) | − | + | + | − | + |
| b-iii) | − | − | − | − | + |
| b-iv) | + | + | + | − | + |
| b-v) | + | + | − | − | + |

A final aspect of the current invention is a method for determining the presence of monomeric anti-drug antibodies in a sample with an immunoassay, wherein the method comprises the following steps:
a) providing
  a-i) a capture drug antibody, which is said drug antibody conjugated to a solid phase,
  a-ii) a tracer drug antibody, which is said drug antibody conjugated to a detectable label,
b) contacting said capture drug antibody separately with
  b-i) said sample,
  b-ii) said sample, to which said drug antibody in monomeric form has been added,
  b-iii) said sample, to which said drug antibody in oligomeric form has been added,
  b-iv) said sample, to which human immunoglobulin G in monomeric form has been added,
  b-v) said sample, to which human immunoglobulin G in oligomeric form has been added,
c) determining the anti-drug antibody in the sample to be of monomeric form by a positive immunoassay in b-i) and b-ii) and b-iv) and a negative immunoassay in b-iii) and b-v).

In one embodiment of the aspects of the invention said immunoassay is a double antigen bridging immunoassay comprising a capture drug antibody and a tracer drug antibody. Another embodiment of the aspects of the invention is that said drug antibody is an antibody for the treatment of an inflammatory disease. In one embodiment said antibody for the treatment of an inflammatory disease is an antibody for the treatment of rheumatoid arthritis or osteoarthritis. In another embodiment said antibody for the treatment of an inflammatory disease is an antibody against the IL-6 receptor, or against the IGF-1 receptor, or the IL-13 receptor 1 alpha. One embodiment of the aspects of the current invention comprises that said capture drug antibody is a mixture of said drug antibody comprising at least two of said drug antibodies that differ in the antibody site at which they are conjugated to the solid phase, and the tracer drug antibody is a mixture of said drug antibody comprising at least two of said drug antibodies that differ in the antibody site at which they are conjugated to the detectable label. A further embodiment is that conjugation of the drug antibody to its conjugation partner is performed by chemically binding via N-terminal and/or ε-amino groups (lysine), ε-amino groups of different lysines, carboxy-, sulfhydryl-, hydroxyl- and/or phenolic functional groups of the amino acid backbone of the drug antibody and/or sugar alcohol groups of the carbohydrate structure of the drug antibody. In an embodiment of the invention's aspects the capture drug antibody mixture or the tracer drug antibody mixture comprises a drug antibody conjugated via an amino group and a drug antibody conjugated via a carbohydrate structure to their conjugation partner. In a further embodiment the conjugation of the capture drug antibody to the solid phase is performed by passive adsorption, or via a specific binding pair. In one embodiment of the invention the specific binding pair (first component/second component) is selected from Streptavidin or Avidin/biotin, or antibody/antigen (see, for example, Hermanson, G. T., et al., Bioconjugate Techniques, Academic Press, 1996), or lectin/polysaccharide, or steroid/steroid binding protein, or hormone/hormone receptor, or enzyme/substrate, or IgG/Protein A and/or G. In one embodiment the capture drug antibody is conjugated to biotin and conjugation to the solid phase is performed via immobilized Avidin or Streptavidin. In one embodiment of the aspects of the current invention the method comprises after step b) an additional step ba) of contacting said capture drug antibody contacted with said sample in step b) with said tracer drug antibody and detecting the detectable label. In still another embodiment of the aspects of the invention the tracer drug antibody is conjugated to the detectable label via a specific binding pair. In one embodiment said tracer drug antibody is conjugated to digoxigenin and linking to the detectable label is performed via an antibody against digoxigenin. Another embodiment of the aspects of the current invention is that the ratio of capture drug antibody to tracer drug antibody is 1:10 to 50:1 (ratio means ratio of antibody molecules irrespective of the molecular weight of the conjugates which can be different).

Another aspect of the current invention is a kit for determining an anti-drug antibody to a drug antibody in a sample comprising:
a) a streptavidin coated micro titer plate,
b) a reagent for conjugation of a drug antibody to biotin,
c) a reagent for conjugation of said drug antibody to digoxigenin,
d) a horseradish peroxidase conjugated anti-digoxigenin antibody,
e) a reagent for oligomerization of said drug antibody,
f) human immunoglobulin G in monomeric form, and
g) human immunoglobulin G in oligomeric form.

A further aspect of the current invention is a method for determining the kind of an antibody to a drug antibody (anti-drug antibody) present in a sample using a double antigen bridging immunoassay comprising a capture drug antibody and a tracer drug antibody, whereby the method comprises the following steps:
a) providing
    a-i) said capture drug antibody, which is said drug antibody conjugated to a solid phase,
    a-ii) said tracer drug antibody, which is said drug antibody conjugated to a detectable label,
b) contacting said capture drug antibody separately with
    b-i) said sample,
    b-ii) said sample, to which said drug antibody in monomeric form has been added,
    b-iii) said sample, to which said drug antibody in oligomeric form has been added,
    b-iv) said sample, to which human immunoglobulin G in monomeric form has been added,
    b-v) said sample, to which human immunoglobulin G in oligomeric form has been added,
c) determining an antibody present in said sample to be a specific, monomeric anti-drug antibody by a positive immunoassay in b-i) and b-iv) and b-v) and a negative immunoassay in b-ii) and b-iii), or
determining an antibody present in said sample to be a specific, oligomeric anti-drug antibody by a positive immunoassay in b-i) and b-ii) and b-iv) and b-v) and a negative immunoassay in b-iii), or
determining an antibody present in said sample to be an unspecific, oligomeric anti-human IgG antibody by a positive immunoassay in b-i) and b-ii) and b-iv) and a negative immunoassay in b-iii) and b-v), or
determining an antibody present in said sample to be an unspecific antibody by a positive immunoassay in b-i) and b-ii) and b-iii) and b-iv) and b-v), or
determining an antibody present in said sample to be an unspecific, monomeric anti-human IgG antibody by a positive immunoassay in b-i) and a negative immunoassay in b-ii) and b-iii) and b-iv) and b-v).

DETAILED DESCRIPTION OF THE INVENTION

The current invention reports a method for determining an antibody against a drug antibody in a sample using an immunoassay comprising a capture drug antibody and a tracer drug antibody, wherein said method comprises the following steps:
a) providing
    a-i) said capture drug antibody, which is said drug antibody conjugated to a solid phase,
    a-ii) said tracer drug antibody, which is said drug antibody conjugated to a detectable label,
b) contacting said capture drug antibody separately with
    b-i) said sample,
    b-ii) said sample, to which said drug antibody in monomeric form has been added,
    b-iii) said sample, to which said drug antibody in oligomeric form has been added,
c) determining an antibody against said drug antibody in said sample by a positive immunoassay in b-i) and a negative immunoassay in b-ii) and b-iii).

The term "drug antibody" according to the invention denotes an antibody which can be administered to an individual, so that a sample of said individual is suspected to comprise said drug antibody after administration. Within one assay performed according to the invention the drug antibody, the capture drug antibody and the tracer drug antibody comprise the "same" antibody molecule, e.g. recombinantly produced with the same expression vector and comprising the same amino acid sequence. Drug antibodies (therapeutic monoclonal antibodies) are being used widely for the treatment of various diseases such as oncological diseases (e.g. hematological and solid malignancies including non-Hodgkin's lymphoma, breast cancer, and colorectal cancer) or inflammatory diseases. Such antibodies are reported, for example, by Levene, A. P., et al., Journal of the Royal Society of Medicine 98 (2005) 145-152; Groner, B., et al., Curr. Mol. Meth. 4 (2004) 539-547; and Harris, M., Lancet Oncol. 5

(2004) 292-302. Exemplary antibodies are, for instance, antibodies against CD20, CD22, HLA-DR, CD33, CD52, EGFR, G250, GD3, HER2, PSMA, CD56, VEGF, VEGF2, CEA, Levis Y antigen, IL-6 receptor, IGF-1 receptor, or IL-13 receptor 1 alpha. In one embodiment said drug antibody is an antibody which is useful for the treatment of an inflammatory disease, i.e. an anti-inflammatory antibody, such as an anti-IL-6 receptor antibody, or an anti-IGF-1 receptor antibody, or an anti-IL-13 receptor 1 alpha antibody.

An example (preferably monoclonal) antibody is an antibody against the IL-6 receptor (mAb IL-6R). Such an antibody is, for example, reported by Mihara, et al., Clin. Immunol. 98 (2001) 319-326; Nishimoto, N., et al, Blood 106 (2005) 2627-2632, in clinical trial NCT00046774, or in WO 2004/096274.

An example (preferably monoclonal) antibody is an antibody against the IGF-1 receptor (mAb IGF-1R). Such an antibody is, for example, reported in WO 2004/087756 or in WO 2005/005635.

An example (preferably monoclonal) antibody is an antibody against the IL-13 receptor alpha (also denoted as mAb IL-13Ral or mAb IL-13R in the following). Antibodies against IL-13Ral are known from, e.g., WO 96/29417, WO 97/15663, WO 03/080675, Graber, P., et al., Eur. J. Immunol. 28 (1998) 4286-4298; Poudrier, J., et al., J. Immunol. 163 (1999) 1153-1161; Poudrier, J., et al., Eur. J. Immunol. 30 (2000) 3157-3164; Aikawa, M., et al., Cytokine 13 (2001) 75-84, and are commercially available from, e.g., R&D Systems Inc. USA. Further exemplary antibodies against IL-13Ral are reported in WO 2006/072564.

The term "anti-drug antibody" as used within this application denotes an antibody, which is directed against, i.e. binds to, an antigenic region of a drug antibody. This antigenic region may be the variable region, a CDR, the constant region, or the glycostructure of the drug antibody. In one embodiment said anti-drug antibody is directed against a CDR region of said drug antibody or a secondary modification of said drug antibody resulting from the recombinant production of said drug antibody in non-human cells, such as, CHO cells, HEK cells, Sp2/0 cells, or BHK cells. Generally anti-drug antibodies are directed against an antigenic region of a drug antibody that is recognized by the immune system of an animal to which the drug antibody is administered. The above described antibodies are termed "specific anti-drug antibody". Drug antibodies are designed to comprise as few as possible antigenic regions. For example, drug antibodies intended for the use in humans are humanized prior to the application to a human patient in order to minimize the generation of an immune response against the drug antibody. This immune response would be in the form of anti-drug antibodies which are directed against the non-human parts of such a humanized drug antibodies, such as e.g. the complementary determining regions in the variable domains (see e.g. Pan, Y., et al., FASEB J. 9 (1995) 43-49).

The term "anti-human IgG antibody" denotes a human antibody directed against any antigenic region of a human or humanized antibody of the antibody class G. Such an anti-human IgG antibody is an example of a "not-specific anti-drug antibody". The term "not-specific anti-drug antibody" denotes within this application an antibody that is binding to the drug antibody but is also binding to a multitude of other antibodies, such as endogenous human antibodies, due to the binding to a common antigenic site that is not determining the drug antibody's specificity.

Antibodies contain as proteins a number of reactive moieties, such as, for example, amino groups (lysines, alpha-amino groups), thiol groups (cystines, cysteine, and methionine), carboxylic acid groups (aspartic acid, glutamic acid) and sugar-alcoholic groups. These can be employed for coupling to a binding partner like a surface, a protein, a polymer (such as e.g. PEG, Cellulose or Polystyrol), an enzyme, or a member of a binding pair (see e.g. Aslam M., and Dent, A., Bioconjuation MacMillan Ref. Ltd. (1999) 50-100).

One of the most common reactive groups of proteins is the aliphatic ε-amine of the amino acid lysine. In general, nearly all antibodies contain abundant lysine. Lysine amines are reasonably good nucleophiles above pH 8.0 ($pK_a$=9.18) and therefore react easily and cleanly with a variety of reagents to form stable bonds. Another common reactive group in antibodies is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulthydryl groups are relatively reactive, proteins with these groups often exist with them in their oxidized form as disulfide groups or disulfide bonds. In addition to cystine and cysteine, some proteins also have the amino acid methionine, which is containing sulfur in a thioether linkage. The literature reports the use of several thiolating crosslinking reagents such as Traut's reagent (2-iminothiolane), succinimidyl(acetylthio) acetate (SATA), or sulfosuccinimidyl 6-[3-(2-pyridyldithio) propionamido]hexanoate (Sulfo-LC-SPDP) to provide efficient ways of introducing multiple sulthydryl groups via reactive amino groups. Reactive esters, particularly N-hydroxysuccinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with protein amines in aqueous solution (optimally at pH 9.0 to 9.5). Aldehydes react under mild aqueous conditions with aliphatic and aromatic amines, hydrazines, and hydrazides to form an imine intermediate (Schiffs base). A Schiffs base can be selectively reduced with mild or strong reducing agents (such as sodium borohydride or sodium cyanoborohydride) to derive a stable alkyl amine bond. Other reagents that have been used to modify amines are acid anhydrides. For example, diethylenetriaminepentaacetic anhydride (DTPA) is a bifunctional chelating agent that contains two amine-reactive anhydride groups. It can react with N-terminal and ε-amine groups of proteins to form amide linkages. The anhydride rings open to create multivalent, metal-chelating arms able to bind tightly to metals in a coordination complex.

Another common reactive group in antibodies is the carboxylic acid group (aspartic acid, glutamic acid). Proteins contain carboxylic acid groups at the C-terminal position and within the side chains of aspartic acid and glutamic acid. For conjugation is the carboxylic acid group usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of other amines on the protein. Protein crosslinking can occur when the pH is raised above 8.0.

Sodium periodate can be used to oxidize the alcohol part of a sugar within a carbohydrate moiety to an aldehyde. Each aldehyde group can be reacted with an amine, hydrazide, or hydrazine as described for carboxylic acids. Since the carbohydrate moiety is predominantly found on the crystallizable fragment (Fc) region of an antibody, conjugation can be achieved through site-directed modification of the carbohydrate away from the antigen-binding site.

Thiol-reactive reagents are those that will couple to thiol groups on proteins, forming thioether-coupled products. These reagents react rapidly at slight acidic to neutral pH and therefore can be reacted selectively in the presence of amine groups. Haloacetyl derivatives, e.g. iodoacetamides, form thioether bonds and are reagents for thiol modification. In antibodies, the reaction takes place at cysteine groups that are either intrinsically present or that result from the reduction of cystine's disulfides at various positions of the antibody. Further useful reagents are maleimides. The reaction of maleimides with thiol-reactive reagents is essentially the same as with iodoacetamides. Maleimides react rapidly at slight acidic to neutral pH.

Amines, hydrazides, and hydrazines are aldehyde and carboxylic acid-reactive reagents (formation of amide, hydrazone, or alkyl amine bonds). Amines, hydrazides, and hydrazines can be coupled to carboxylic acids of proteins after the activation of the carboxyl group by a water-soluble carbodiimide. The amine-containing reagent must be weakly basic so that it reacts selectively with the carbodiimide-activated protein in the presence of the more highly basic ε-amines of lysine to form a stable amide bond. In the reaction with aldehyde groups, which can be generated on antibodies by periodate oxidation of the carbohydrate residues on the antibody, a Schiff's base intermediate is formed, which can be reduced to an alkyl amine through the reduction of the intermediate with sodium cyanoborohydride (mild and selective) or sodium borohydride (strong) water-soluble reducing agents.

The term "sample" as used within this application denotes, but is not limited to, any quantity of a substance from a living thing or formerly living thing. Such living things include, but are not limited to, humans, mice, monkeys, rats, rabbits, and other animals. Such substances include, but are not limited to, whole blood, serum or plasma from an individual, which are the most widely used sources of sample in clinical routine.

The term "solid phase" as used within this application denotes a non-fluid substance, and includes particles (including microparticles and beads) made from materials such as polymer, metal (paramagnetic or ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component of an assay is distinguished from inert solid surfaces with which the assay may be in contact in that a "solid phase" contains at least one moiety on its surface, which is intended to interact with the capture drug antibody. A solid phase may be a stationary component, such as a tube, strip, cuvette or microtiter plate, or may be non-stationary components, such as beads and microparticles. Microparticles can also be used as a solid phase for homogeneous assay formats. A variety of microparticles that allow both non-covalent or covalent attachment of proteins and other substances may be used. Such particles include polymer particles, such as polystyrene and poly(methylmethacrylate); gold particles, such as gold nanoparticles and gold colloids; and ceramic particles, such as silica, glass, and metal oxide particles. See for example Martin, C. R., et al., Analytical Chemistry-News & Features (1998) 322A-327A, which is incorporated herein by reference. Solid supports for the immunoassays according to the invention are widely described in the state of the art (see, e.g., Butler, J. E., Methods 22 (2000) 4-23).

Chromogens (fluorescent or luminescent groups and dyes), enzymes, NMR-active groups or metal particles, haptens, e.g. digoxigenin, are examples of detectable labels. The detectable label can also be a photoactivatable crosslinking group, e.g. an azido or an azirine group. Metal chelates which can be detected by electrochemoluminescence are also detectable signal-emitting groups, with particular preference being given to ruthenium chelates, e.g. a ruthenium $(bispyridyl)_3^{2+}$ chelate. Suitable ruthenium labeling groups are described, for example, in EP 0 580 979, WO 90/005301, WO 90/11511, and WO 92/14138.

Samples, in which an antibody is to be determined, often contain more than the antibody in question. Thus, it cannot be avoided that the determination by an immunoassay results in a positive immunoassay albeit the sample does not contain said antibody to be determined. In order to use such an assay such positive immunoassays have to be excluded or at least reduced to an acceptable ration, e.g. below 5% of all positive immunoassays.

It has now surprisingly been found that positive immunoassays of a sample to be analyzed by a method for determining an antibody against a drug antibody (anti-drug antibody, ADA) can be identified by spiking the sample to be analyzed with drug antibody and non-specific antibody and by determining the result of the method with these spiked samples.

The term "spiked" as used within this application denotes that to the sample to be analyzed a supplementary substance is added, which may or may not already be present in said sample. The supplementation of the substance has the effect that said substance is present in said sample in a concentration which exceeds the concentration of the anti-drug antibody in question in said sample. In one embodiment said supplementary substance is an antibody, in another embodiment it is said drug antibody or an Fc-part specific antibody, such as an anti-human IgG antibody.

The term "antibody" as used herein encompasses the various forms of antibody structures including whole antibodies and antibody fragments. In one embodiment the drug antibody in the method according to the invention is a human antibody, a humanized antibody, a chimeric antibody, or a T cell antigen depleted antibody (see e.g. WO 98/33523, WO 98/52976, or WO 00/34317). Genetic engineering of antibodies is e.g. reported by Morrison, S. L., et al., Proc. Natl. Acad. Sci. USA 81 (1984) 6851-6855; U.S. Pat. No. 5,202,238 and U.S. Pat. No. 5,204,244; Riechmann, L., et al., Nature 332 (1988) 323-327; Neuberger, M. S., et al., Nature 314 (1985) 268-270; Lonberg, N., Nat. Biotechnol. 23 (2005) 1117-1125.

An "antibody fragment" denotes a fragment of a complete antibody which has retained the ability to bind to the same antigen as the complete antibody. A "complete antibody" is an antibody consisting of two light polypeptide chains and to heavy polypeptide chains, each of them comprising a variable region and a constant region. An "antibody conjugate" denotes a conjugate of an antibody with a further polypeptide. The binding of the antigen is not diminished by the conjugation to the further polypeptide. "Antibody fragments" comprise a portion of a full length antibody, preferably the variable domains thereof or at least the antigen binding portion thereof. Examples of antibody fragments are single-chain antibody molecules (scFv), Fab, $F(ab)_2$ fragments, and the like, as long as they retain the binding characteristics of the antibody. ScFv antibodies are, e.g., reported in Huston, J. S., Methods in Enzymol. 203 (1991) 46-88. Huston also reports linkers and methods for linking of polypeptides useful for the present invention.

The "Fc part" of an antibody is not involved directly in binding to the antigen, but exhibit various effector functions. Depending on the amino acid sequence of the constant region of the heavy chains, antibodies (immunoglobulins) are divided in the classes: IgA, IgD, IgE, IgG, and IgM. Some of these classes are further divided into subclasses (isotypes), i.e. IgG in IgG1, IgG2, IgG3, and IgG4, or IgA in IgA1 and IgA2. According to the immunoglobulin class to which an antibody belongs the heavy chain constant regions of immunoglobulins are called α (IgA), δ (IgD), ε (IgE), γ (IgG), and μ (IgM), respectively. The drug antibody in the methods according to the invention belongs in one embodiment to the IgG class. An "Fc part of an antibody" is a term well known to the skilled artisan and defined on basis of the papain cleavage of the antibody.

The term "antibody" as used herein refers to a protein consisting of one or more polypeptides substantially encoded by antibody genes. The different polypeptides of which an antibody is composed of are referred to depending on their weight as light polypeptide chain and as heavy polypeptide chain. The recognized antibody genes include the different constant region genes as well as the myriad antibody variable region genes. Antibodies may exist in a variety of formats, including, for example, single heavy and light chains, Fv, Fab, and F(ab)$_2$ as well as single chains (scFv) (e.g. Huston, J. S., et al., Proc. Natl. Acad. Sci. USA 85 (1988) 5879-5883; Bird, R. E., et al., Science 242 (1988) 423-426; in general, Hood, L., et al., Immunology, Benjamin N.Y., 2nd edition (1984); Hunkapiller, T., and Hood, L., Nature 323 (1986) 15-16).

An antibody in general comprises two light polypeptide chains and two heavy polypeptide chains. Each of the heavy and light polypeptide chain contains a variable region (the amino terminal portion of the polypeptide chain) which contains a binding domain that is able to interact with an antigen. Each of the heavy and light polypeptide chain comprises a constant region (the carboxyl terminal portion of the polypeptide chain). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. The variable domain of an antibody's light or heavy chain in turn comprises different segments, i.e. four framework regions (FR) and three hypervariable regions (CDR).

"Humanized" forms of non-human (e.g. rodent) antibodies are antibodies that contain partial sequences derived from a non-human antibody and from a human antibody. For the most part, humanized antibodies are derived from a human antibody (recipient antibody), in which residues from a hypervariable region are replaced by residues from a hypervariable region of a non-human species (donor antibody), such as mouse, rat, rabbit, or non-human primate, having the desired specificity and affinity (see e.g. Morrison, S. L., et al., Proc. Natl. Acad. Sci. USA 81 (1984) 6851-6855; U.S. Pat. No. 5,202,238; U.S. Pat. No. 5,204,244). In some instances, framework region (FR) residues of the human antibody are replaced by corresponding non-human residues. Furthermore, humanized antibodies may comprise further modifications, e.g. amino acid residues that are not found in the recipient antibody or in the donor antibody. Such modifications result in variants of such recipient or donor antibody, which are homologous but not identical to the corresponding parent sequence. These modifications are made to further refine antibody performance. In general, the humanized antibody will comprise substantially all of at least one, and typically two, variable domains, in which all or substantially all of the hypervariable loops correspond to those of a non-human donor antibody and all or substantially all of the FRs are those of a human recipient antibody. The humanized antibody optionally will also comprise at least a portion of an antibody constant region, typically that of a human antibody. Methods for humanizing non-human antibody have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers by substituting hypervariable region sequences for the corresponding sequences of a non-human antibody. Accordingly, such "humanized" antibodies are antibodies, wherein substantially less than an intact human variable domain has been substituted by the corresponding sequence from a non-human species. In practice, humanized antibodies are typically human antibodies in which some hypervariable region residues and possibly some framework region residues are substituted by residues from analogous sites in rodent or non-human primate antibodies.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which include different antibodies directed against different antigenic sites (determinants or epitopes), each monoclonal antibody is directed against a single antigenic site on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies and is not to be construed as requiring production of the antibody by any particular method.

The term "antibody in monomeric form" as used within this application denotes that said antibody is not associated either covalently or non-covalently with further antibody molecules of the same specificity. For example, an anti-IGF-1R antibody is in monomeric form if it is not associated with a second anti-IGF-1R antibody. This does not exclude that said antibody may be associated either covalently or non-covalently with other antibodies such as e.g. an anti-IL-6R antibody.

The term "antibody in oligomeric form" as used within this application denotes that said antibody is associated either covalently or non-covalently with further antibody molecules of the same specificity. In one embodiment the "antibody in oligomeric form" is covalently associated with one or more further antibody molecules of the same specificity. For example, an anti-IGF-1R antibody is in oligomeric form if it is associated with at least a second anti-IGF-1R antibody.

The term "same specificity" as used within this application denotes that two antibodies bind the same target molecule, i.e. the same antigen. This does not exclude that the two antibodies bind to different epitopes of said antigen. In one embodiment the antibodies comprised in an antibody in oligomeric from do bind to the same antigen and to the same epitope. In another embodiment said antibodies in an antibody in an oligomeric form are the same monoclonal antibody.

The first aspect of the current invention is a method for determining an antibody against a drug antibody in a sample using an immunoassay comprising a capture drug antibody and a tracer drug antibody, wherein said method comprises the following steps:
a) providing
   a-i) said capture drug antibody, which is said drug antibody conjugated to a solid phase,
   a-ii) said tracer drug antibody, which is said drug antibody conjugated to a detectable label,
b) contacting said capture drug antibody separately with
   b-i) said sample,
   b-ii) said sample, to which said drug antibody in monomeric form has been added prior to the immunoassay,
   b-iii) said sample, to which said drug antibody in oligomeric form has been added prior to the immunoassay,
c) determining an antibody against said drug antibody in said sample by a positive immunoassay in b-i) and a negative immunoassay in b-ii) and b-iii).

This method is especially useful if the sample contains antibodies other than the anti-drug antibody in question which can interfere in immunoassays for the detection of said anti-drug antibody and, thus, result in a positive immunoassay. In one embodiment the methods of the current invention are useful for the determination of anti-drug antibodies of drug antibodies used for an anti-inflammatory therapy. The term "drug antibodies used for an anti-inflammatory therapy" as used within this application denotes that said drug antibody is directed against a cell surface receptor that mediates inflammation. Such receptors are for example the IL-6 receptor, or the IGF-1 receptor, or the IL-13a receptor 1. If a sample from a subject, which is treated with such an anti-inflammatory drug antibody, is analyzed, it has to be determined, whether the positive result of the method is based on an anti-drug antibody or on an antibody other than an anti-drug antibody of the sample. An example of such a case is a sample from a subject, which has an autoimmune disease such as rheumatism, and thus a sample obtained from said subject contains so called "rheumatic factors". The term "rheumatic factors" as used within this application denotes antibodies binding to human IgG, to be more precisely to the Fc-part of human IgG. In most cases these "rheumatic factors" are oligomeric binding molecules.

Thus, it has surprisingly been found that the interference of such anti-human IgG antibodies can be determined by the spiking the sample to be analyzed with defined antibodies, either in monomeric or in oligomeric form, and performing the method for determining an anti-drug antibody with said spiked sample and based on the result of the method performed with the different samples determining whether the immunoassay is positive or not.

Another aspect of the current invention is a method for determining whether an antibody present in a sample is an anti-drug antibody or an anti-human IgG antibody, i.e. whether an antibody present in the sample is an specific anti-drug antibody or a not-specific anti-drug antibody, using a double antigen bridging immunoassay comprising a capture drug antibody and a tracer drug antibody, wherein said method comprises the following steps:
a) providing
   a-i) said capture drug antibody, which is said drug antibody conjugated to a solid phase,
   a-ii) said tracer drug antibody, which is said drug antibody conjugated to a detectable label,
b) contacting said capture drug antibody separately with
   b-i) said sample,
   b-ii) said sample, to which said drug antibody in monomeric form has been added prior to the immunoassay,
   b-iii) said sample, to which said drug antibody in oligomeric form has been added prior to the immunoassay,
   b-iv) said sample, to which human IgG in monomeric form has been added prior to the immunoassay,
   b-v) said sample, to which human IgG in oligomeric form has been added prior to the immunoassay,
c) determining an antibody present in said sample to be an anti-drug antibody by a positive immunoassay in b-i) and b-iv) and b-v) and a negative immunoassay in b-ii) and b-iii), or
determining an antibody present in said sample to be an anti-human IgG antibody by a positive immunoassay in b-i) and b-ii) and b-iv) and a negative immunoassay in b-iii) and b-v).

The terms "positive immunoassay" and "positive immunoassay result", which are use interchangeably within this application, denotes in case of the immunoassay performed with said not supplemented sample, that the immunoassay performed with said not supplemented sample yields a signal well above the background level of said immunoassay. In one embodiment said background level is the mean signal obtained by the determination of a multitude of samples from different individuals, to whom said drug antibody had not been administered, in said immunoassay plus three times the standard deviation of the mean value, i.e. a 95% confidence interval. Likewise denote the terms "negative immunoassay" and "negative immunoassay result" which are use interchangeably within this application a signal within the background level of said immunoassay, i.e. within three times the standard deviation of the signal obtained with a sample without any antibody in said immunoassay.

The terms "positive immunoassay" and "positive immunoassay result", which are use interchangeably within this application, denotes in case of the immunoassay performed with said supplemented sample as used within this application, that the immunoassay performed with said supplemented sample yields in one embodiment a relative signal of 50% or more, in another embodiment of 65% or more, in still another embodiment of 80% or more, of said signal in case of the immunoassay performed with said not-supplemented sample. The term "negative immunoassay" denotes in case of the immunoassay performed with said supplemented sample as used within this application, that the immunoassay performed with said supplemented sample yields in one embodiment a relative signal of less than 50% of said signal, in another embodiment of less than 65% of said signal, in still another embodiment of less than 80% of said signal, in case of the immunoassay performed with said not-supplemented sample.

The immunoassay according to the invention comprises the following steps in the following order:
a) contacting the capture drug antibody conjugated to a solid phase with said unspiked or spiked sample,
b) contacting said capture drug antibody conjugated to a solid phase that has been contacted with the sample with the tracer drug antibody,
c) detecting the tracer drug antibody by detecting the detectable label conjugated to the tracer drug antibody.

Optionally wash steps may be included between steps a) and b), and b) and c).

A "positive immunoassay" and "positive immunoassay result" is obtained when
   a) an anti-drug antibody contained in the sample is bound to the solid phase by the capture drug antibody,
   b) the tracer drug antibody binds to the complex of a), and c) the detectable label of the tracer drug antibody is detected either directly or with the help of a further binding partner.

In case of a "negative immunoassay" or "negative immunoassay result" one or more of the above listed criteria are not met.

The third aspect of the current invention is a method for distinguishing in a sample an anti-drug antibody to a humanized anti-inflammatory drug antibody from an anti-human IgG antibody, i.e. to distinguish a specific anti-drug antibody from a not-specific anti-drug antibody, wherein the method comprises the following steps:
a) providing
   a-i) a capture drug antibody, which is said drug antibody conjugated to a solid phase,
   a-ii) a tracer drug antibody, which is said drug antibody conjugated to a detectable label,
b) contacting said capture drug antibody separately with
   b-i) said sample,
   b-ii) said sample, to which said drug antibody in monomeric form has been added prior to the immunoassay,
   b-iii) said sample, to which said drug antibody in oligomeric form has been added prior to the immunoassay,
   b-iv) said sample, to which human immunoglobulin G in monomeric form has been added prior to the immunoassay,
   b-v) said sample, to which human immunoglobulin G in oligomeric form has been added prior to the immunoassay,
c) determining an anti-drug antibody to a humanized anti-inflammatory drug antibody by a positive immunoassay in b-i) and b-iv) and b-v) and a negative immunoassay in b-ii) and b-iii), or
determining an antibody present in said sample to be an anti-human IgG antibody by a positive immunoassay in b-i) and b-ii) and b-iv) and a negative immunoassay in b-iii) and b-v).

Still a further aspect of the current invention is a method for determining whether an anti-drug antibody in a sample is of monomeric or oligomeric form, wherein the method comprises the following steps:
a) providing
   a-i) a capture drug antibody, which is said drug antibody conjugated to a solid phase,
   a-ii) a tracer drug antibody, which is said drug antibody conjugated to a detectable label,
b) contacting said capture drug antibody separately with
   b-i) said sample,
   b-ii) said sample, to which said drug antibody in monomeric form has been added prior to the immunoassay,
   b-iii) said sample, to which said drug antibody in oligomeric form has been added prior to the immunoassay,
   b-iv) said sample, to which human immunoglobulin G in monomeric form has been added prior to the immunoassay,
   b-v) said sample, to which human immunoglobulin G in oligomeric form has been added prior to the immunoassay,
c) determining the anti-drug antibody in the sample to be of monomeric form by a positive immunoassay in b-i) and b-ii) and b-iv) and a negative immunoassay in b-iii) and b-v), or determining an anti-drug antibody in a sample is of oligomeric form by a positive immunoassay in b-i) and b-iii) and b-v) and a negative immunoassay in b-ii) and b-iv).

Another aspect of the current invention is a method for determining the presence of oligomeric anti-drug antibodies in a sample, wherein the method comprises the following steps:
a) providing
   a-i) a capture drug antibody, which is said drug antibody conjugated to a solid phase,
   a-ii) a tracer drug antibody, which is said drug antibody conjugated to a detectable label,
b) contacting said capture drug antibody separately with
   b-i) said sample,
   b-ii) said sample, to which said drug antibody in monomeric form has been added prior to the immunoassay,
   b-iii) said sample, to which said drug antibody in oligomeric form has been added prior to the immunoassay,
   b-iv) said sample, to which human immunoglobulin G in monomeric form has been added prior to the immunoassay,
   b-v) said sample, to which human immunoglobulin G in oligomeric form has been added prior to the immunoassay,
c) determining the anti-drug antibody in a sample to be of oligomeric form by a positive immunoassay in b-i) and b-iii) and b-v) and a negative immunoassay in b-ii) and b-iv).

Another aspect of the current invention is a method for determining the presence of a monomeric anti-drug antibody in a sample, wherein the method comprises the following steps:
a) providing
   a-i) a capture drug antibody, which is said drug antibody conjugated to a solid phase,
   a-ii) a tracer drug antibody, which is said drug antibody conjugated to a detectable label,
b) contacting said capture drug antibody separately with
   b-i) said sample,
   b-ii) said sample, to which said drug antibody in monomeric form has been added prior to the immunoassay,
   b-iii) said sample, to which said drug antibody in oligomeric form has been added prior to the immunoassay,
   b-iv) said sample, to which human immunoglobulin G in monomeric form has been added prior to the immunoassay,
   b-v) said sample, to which human immunoglobulin G in oligomeric form has been added prior to the immunoassay,
c) determining the anti-drug antibody in the sample to be of monomeric form by a positive immunoassay in b-i) and b-ii) and b-iv) and a negative immunoassay in b-iii) and b-v).

It has now surprisingly been found that with the supplementation of said sample with said drug antibody in monomeric and in oligomeric form as well as with human IgG in monomeric and in oligomeric form a pattern of assay results can be obtained from which the determination of the class of the result can be performed, which is depicted in the following scheme:

|  | specific, monomeric response | specific, oligomeric response | unspecific, oligomeric response | unspecific, monomeric response |
|---|---|---|---|---|
| sample, b-i) | + | + | + | + |
| b-ii) | − | + | + | − |
| b-iii) | − | − | − | − |
| b-iv) | + | + | + | − |
| b-v) | + | + | − | − |

Therefore, with the method according to the invention specific and not-specific as well as monomeric and oligomeric immunoassay responses or results can be classified.

Thus, the current invention comprises as a further aspect a method for determining a positive result of a determination of an antibody against a drug antibody in a sample using an immunoassay comprising a capture drug antibody and a tracer drug antibody, wherein said method comprises the following steps:
a) providing
  a-i) a capture drug antibody, which is said drug antibody conjugated to a solid phase,
  a-ii) a tracer drug antibody, which is said drug antibody conjugated to a detectable label,
b) contacting said capture drug antibody separately with
  b-i) said sample,
  b-ii) said sample, to which said drug antibody in monomeric form has been added prior to the immunoassay,
  b-iii) said sample, to which said drug antibody in oligomeric form has been added prior to the immunoassay,
  b-iv) said sample, to which human immunoglobulin G in monomeric form has been added prior to the immunoassay,
  b-v) said sample, to which human immunoglobulin G in oligomeric form has been added prior to the immunoassay,
c) determining a positive result of a determination of an antibody against a drug antibody in a sample using an immunoassay by a positive immunoassay in b-i) and b-iii) and b-v) and a negative immunoassay in b-ii) and b-iv).

One embodiment of the aspects of the current invention is that said immunoassay is a double antigen bridging immunoassay using a capture drug antibody and a tracer drug antibody. Another embodiment of the aspects of the invention is that said drug antibody is an antibody for the treatment of an inflammatory disease. In one embodiment said antibody for the treatment of an inflammatory disease is an antibody for the treatment of rheumatoid arthritis or osteoarthritis. In another embodiment said antibody for the treatment of an inflammatory disease is an antibody against the IL-6 receptor, or against the IGF-1 receptor, or the IL-13 receptor 1 alpha. One embodiment of the aspects of the current invention comprises that said capture drug antibody is a mixture of said drug antibody comprising at least two of said drug antibodies that differ in the antibody site at which they are conjugated to the solid phase, and the tracer drug antibody is a mixture of said drug antibody comprising at least two of said drug antibodies that differ in the antibody site at which they are conjugated to the detectable label. A further embodiment is that conjugation of the drug antibody to its conjugation partner is performed by chemically binding via N-terminal and/or ∈-amino groups (lysine), ∈-amino groups of different lysines, carboxy-, sulthydryl-, hydroxyl- and/or phenolic functional groups of the amino acid backbone of the drug antibody and/or sugar alcohol groups of the carbohydrate structure of the drug antibody. In an embodiment of the invention's aspects the capture drug antibody mixture or tracer drug antibody mixture comprises the drug antibody conjugated via an amino group and via a carbohydrate structure to their conjugation partner. In a further embodiment the conjugation of the capture drug antibody to the solid phase is performed by passive adsorption, or via a specific binding pair. In an embodiment of the invention the specific binding pair (first component/second component) is Streptavidin or Avidin/biotin, or antibody/antigen (see, for example, Hermanson, G. T., et al., Bioconjugate Techniques, Academic Press, 1996), or lectin/polysaccharide, or steroid/steroid binding protein, or hormone/hormone receptor, or enzyme/substrate, or IgG/Protein A and/or G. In one embodiment the capture drug antibody is conjugated to biotin and conjugation to the solid phase is performed via immobilized Avidin or Streptavidin. In still another embodiment of the aspects of the invention the tracer drug antibody is conjugated to the detectable label via a specific binding pair, in one embodiment the tracer drug antibody is conjugated to digoxigenin and linking to the detectable label is performed via an antibody against digoxigenin. In another embodiment of the aspects of the current invention the ratio of capture drug antibody to tracer drug antibody is 1:10 to 50:1 (ratio means ratio of antibody molecules irrespective of the molecular weight of the conjugates which can be different).

Another aspect of the current invention is a method for determining the kind of an immune system response to an applied drug antibody, especially a therapeutic antibody. With this method it is possible do distinguish if a detected anti-drug antibody is one of the following:
  i) a specific, monomeric anti-drug antibody, or
  ii) a specific, oligomeric anti-drug antibody, or
  iii) an unspecific, oligomeric anti-human IgG antibody, or
  iv) an unspecific, monomeric anti-human IgG antibody, or
  v) an unspecific antibody.

Therefore, the current invention comprises a method for determining the kind of an antibody to a drug antibody (anti-drug antibody) present in a sample using a double antigen bridging immunoassay comprising a capture drug antibody and a tracer drug antibody, whereby the method comprises the following steps:
a) providing
  a-i) said capture drug antibody, which is said drug antibody conjugated to a solid phase,
  a-ii) said tracer drug antibody, which is said drug antibody conjugated to a detectable label,
b) contacting said capture drug antibody separately with
  b-i) said sample,
  b-ii) said sample, to which said drug antibody in monomeric form has been added prior to the immunoassay,
  b-iii) said sample, to which said drug antibody in oligomeric form has been added prior to the immunoassay,
  b-iv) said sample, to which human immunoglobulin G in monomeric form has been added prior to the immunoassay,
  b-v) said sample, to which human immunoglobulin G in oligomeric form has been added prior to the immunoassay,
c) determining an antibody present in said sample to be a specific, monomeric anti-drug antibody by a positive immunoassay in b-i) and b-iv) and b-v) and a negative immunoassay in b-ii) and b-iii), or
determining an antibody present in said sample to be a specific, oligomeric anti-drug antibody by a positive immunoassay in b-i) and b-ii) and b-iv) and b-v) and a negative immunoassay in b-iii), or
determining an antibody present in said sample to be an unspecific, oligomeric anti-human IgG antibody by a positive immunoassay in b-i) and b-ii) and b-iv) and a negative immunoassay in b-iii) and b-v), or
determining an antibody present in said sample to be an unspecific antibody by a positive immunoassay in b-i) and b-ii) and b-iii) and b-iv) and b-v), or
determining an antibody present in said sample to be an unspecific, monomeric anti-human IgG antibody by a positive immunoassay in b-i) and a negative immunoassay in b-ii) and b-iii) and b-iv) and b-v).

The following examples, references, and figures are provided to aid the understanding of the present invention, the true scope of which is set forth in the appended claims. It is understood that modifications can be made in the procedures set forth without departing from the spirit of the invention.

DESCRIPTION OF FIGURE

FIG. 1 Bridging assay for detection of anti-drug antibodies: The biotinylated drug antibody (Capture-BI) is bound to a Streptavidin-coated microtiter plate (SA-MTP); the anti-drug antibody bridges the capture drug antibody (Capture-BI; BI=biotinylated) with digoxigenin-labeled tracer drug antibody (Tracer-DIG; DIG=digoxigenylated); the immobilized complex is detected by polyclonal anti-digoxigenin horseradish peroxidase conjugate (DIG-pAb-POD); polyclonal rabbit anti-drug antibody (rpAb) is used as standard.

EXAMPLES

Example 1

Biotinylation of Antibody mAb IL-6R with D-Biotinoyl-Aminocaproic Acid-N-Hydroxysuccinimide Ester Antibody against IL-6 receptor (mAb IL-6R) has been dialyzed against buffer (100 mM potassium phosphate buffer (in the following denoted as K—$PO_4$), pH 8.5). Afterwards the solution was adjusted to a protein concentration of 10 mg/ml. D-biotinoyl-aminocaproic acid-N-hydroxysuccinimide ester was dissolved in DMSO and added to the antibody solution in a molar ratio of 1:5. After 60 minutes the reaction was stopped by adding L-lysine. The surplus of the labeling reagent was removed by dialysis against 25 mM K—$PO_4$ supplemented with 150 mM NaCl, pH 7.5.

Example 2

Biotinylation of mAb IL-6R with D-Biotinoyl-Aminocaproic Acid-N-Hydroxysuccinimide Ester after Treatment with Citraconic Acid Anhydride MAb IL-6R has been dialyzed against 100 mM K—$PO_4$, pH 8.4. Afterwards the solution was adjusted to a protein concentration of 20 mg/ml. Citraconic acid anhydride was dissolved in DMSO and added to the antibody solution in a molar ratio of 1:5. After 120 minutes the reaction was stopped by chromatography on a column with Sephadex® G25 equilibrated with 100 mM K—$PO_4$, pH 8.4. The antibody solution was adjusted to a protein concentration of about 4 mg/ml. D-biotinoyl-aminocaproic acid-N-hydroxysuccinimide ester was dissolved in DMSO and added to the antibody solution in a molar ratio of 1:5. The reaction was stopped after 60 minutes by adding L-lysine. The surplus of the labeling reagent was removed by dialysis against 200 mM sodium acetate buffer, pH 5.0. The antibody solution was transferred to a 25 mM K—$PO_4$ supplemented with 150 mM NaCl, pH 7.2, by chromatography on a column with Sephadex® G25.

Example 3

Biotinylation of mAb IL-6R with Biotin Hydrazide

MAb IL-6R has been dialyzed against 100 mM sodium acetate buffer, pH 5.5. Afterwards the solution was adjusted to a protein concentration of 20 mg/ml. Sodium periodate was dissolved in 100 mM sodium acetate buffer, pH 5.5, and was added to the antibody solution to a final concentration of 10 mM. The reaction was stopped after 30 minutes by chromatography on a Sephadex® G25 column equilibrated with 100 mM sodium acetate buffer, pH 5.5. The antibody solution was adjusted to a protein concentration of about 5 mg/ml. Biotin hydrazide was dissolved in DMSO and added to the antibody solution in a molar ratio of 1:50. The reaction was stopped after 120 minutes by adding sodium borohydride to a final concentration of 15 mM. After 30 minutes the antibody solution was dialyzed against 25 mM K—$PO_4$ supplemented with 150 mM NaCl, pH 7.2

Example 4

Digoxigenylation of mAb IL-6R with Digoxigenin 3-O-Methylcarbonyl-ε-Aminocaproic Acid-N-Hydroxysuccinimide Ester MAb IL-6R has been dialyzed against Digoxigenylation buffer (100 mM K—$PO_4$, pH 8.5). Afterwards the solution was adjusted to a protein concentration of 10 mg/ml. Digoxigenin 3-O-methylcarbonyl-ε-aminocaproic acid-N-hydroxysuccinimide ester was dissolved in DMSO and added to the antibody solution in a molar ratio of 1:5. After 60 minutes the reaction has been stopped by adding L-lysine. The surplus of labeling reagent was removed by dialysis against 25 mM K—$PO_4$ supplemented with 150 mM NaCl, pH 7.5.

Example 5

Digoxigenylation of mAb IL-6R with Digoxigenin 3-O-Methylcarbonyl-ε-Aminocaproic Acid-N-Hydroxysuccinimide Ester after Treatment with Citraconic Acid Anhydride MAb IL-6R has been dialyzed against 100 mM K—PO4, pH 8.4. Afterwards the solution was adjusted to a protein concentration of 20 mg/ml. Citraconic acid anhydride was dissolved in DMSO and added to the antibody solution in a molar ratio of 1:5. The reaction has been stopped after 120 minutes by chromatography on a column with Sephadex® G25 equilibrated with 100 mM K—PO4, pH 8.4. The antibody solution was adjusted to a protein concentration of about 4 mg/ml. Digoxigenin 3-O-methylcarbonyl-ε-aminocaproic acid-N-hydroxysuccinimide ester was dissolved in DMSO and added to the antibody solution in a molar ratio of 1:5. The reaction has been stopped after 60 minutes by adding L-lysine. The surplus of the labeling reagent was removed by dialysis against 200 mM sodium acetate buffer, pH 5.0. The antibody solution was transferred to a buffer with 25 mM K—PO4 and 150 mM NaCl, pH 7.2, by chromatography on a column with Sephadex® G25.

Example 6

Digoxigenylation of mAb IL-6R with Digoxigenin-X-Hydrazide

MAb IL-6R has been dialyzed against 100 mM sodium acetate buffer, pH 5.5. Afterwards the solution was adjusted to a protein concentration of 20 mg/ml. Sodium periodate was dissolved in 100 mM sodium acetate buffer, pH 5.5, and was added to the antibody solution to a final concentration of 10 mM. The reaction has been stopped after 30 minutes by chromatography on a Sephadex® G25 column equilibrated with 100 mM sodium acetate buffer, pH 5.5. The antibody solution was adjusted to a protein concentration of about 5 mg/ml. Digoxigenin-X-hydrazide was dissolved in DMSO and added to the antibody solution in a molar ratio of 1:50. After 120 minutes the reaction has been stopped by adding sodium borohydride to a final concentration of 15 mM. After 30 minutes the antibody solution was dialyzed against 25 mM K—PO$_4$ supplemented with 150 mM NaCl, pH 7.2

Example 7 a) Generation of Drug Antibody in Oligomeric Form

The recombinant drug antibody (IgG), e.g. anti-IL-6R antibody, anti-IGF-1R antibody, or anti-IL-13R antibody, was dialyzed against 150 mM potassium phosphate buffer supplemented with 100 mM NaCl, pH 8.4, and afterwards the antibody solution was concentrated to an antibody concentration of 55 mg/ml.

Disuccinimidylsuberate (DSS) was dissolved in DMSO and added to the antibody solution in a molar ration of 1:7 (IgG:DSS). The mixture was incubated at 25° C. and pH 8.4 with stirring and the reaction is analyzed with an analytical gel filtration chromatography (e.g. using a TSK 4000 column). The polymerization was stopped usually after 60 min. by adding lysine to a final concentration of 10 mM. After 45 min. of incubation at 25° C. the polymerized drug antibody was separated by gel filtration (e.g. using a Sephacryl S400 column) to remove low molecular fractions.

b) Generation of Human IgG in Oligomeric Form

Human IgG purified from human serum by ion exchange chromatography was dialyzed against 150 mM potassium phosphate buffer containing 100 mM NaCl, pH 8.4, and the protein solution was concentrated to a protein concentration of 75 mg/ml. Disuccinimidylsuberate (DSS) was dissolved in DMSO and added to the antibody solution in a molar ration of 1:5 (IgG:DSS). The mixture was incubated at 25° C. and pH 8.4 with stirring and the reaction was analyzed with an analytical gel filtration column (e.g. using a TSK 4000 column). The polymerization was stopped usually after 60 min. by adding lysine to a final concentration of 10 mM. After 45 min incubation at 25° C. the oligomeric human IgG was separated by gel filtration (e.g. using a Sephacryl S400 column) to remove low molecular fractions.

Example 8

Assay Principle

The ELISA utilizes immobilized drug antibody (Capture-BI) on Streptavidin microtiter plates (SA-MTP) for the capture of sample containing anti-drug antibodies (ADA). The captured ADA is detected by digoxygenylated drug antibody (Tracer-DIG). The bound complex of ADA and Tracer-DIG is detected by a peroxidase-conjugated polyclonal anti-DIG antibody reacting with its substrate ABTS (2,2'-azino-bis(3-ethylbenzthiazoline-6-sulphonic acid)) and subsequent photometric readout. Optical density (OD) is measured at 405 nm (with 490 nm reference wave length). For the determination of a standard curve the sample is replaced by a solution of an anti-drug antibody at a defined concentration. The highest standard concentration has to reach an OD value of 1.8-2.2 AU.

In the first step, all samples were screened for being positive or negative for anti-drug antibodies (ADAs) (screening assay; yes/no answer) by testing all samples at a dilution of 1:20. The positive/negative cut-point was determined at the 95% confidence interval using the assay response, i.e. the optical density (OD) from multiple analyses of blank serum samples.

In a second step, all positive samples were tested again by using at maximum four additional distinguishing steps to characterize the response (e.g. drug-specificity):
i) unspiked sample
ii) spiking the sample with 1 μg/ml drug antibody in monomeric form
iii) spiking the sample with 1 μg/ml drug antibody in oligomeric form
iv) spiking the sample with 1 μg/ml human IgG in monomeric form
v) spiking the sample with 1 μg/ml human IgG in oligomeric form In the distinguishing steps the ELISA was performed again as described above (screening assay), but the sample was prior to the application to the micro titer plate incubated each with the solutions ii) to v) as described above for the four distinguishing steps. The spiked substances compete with the Capture-BI for binding to substances (e.g. ADA) of the sample. The assay signal of unspiked sample has to be within the dynamic range of the assay, otherwise the sample has to be further diluted. This final sample-dilution has to be also used in all distinguishing steps. If the decrease in absorbance due to the presence of spiked reagents (ii)-v)) is less than 20%, the test result was considered "positive" (positive immunoassay). If the decrease in absorbance was 20% or more, the test result was considered "negative" (negative immunoassay). With other words, if the signal recovery was more than 80%, the test result was considered "positive" (positive immunoassay) and if signal recovery was less than 80%, the test result was considered "negative" (negative immunoassay).

Example 9

ELISA for Detection of Anti-IL-6R-Antibody Antibodies

The assay has been performed according to Example 8. Exception: the sample (spiked or unspiked) was pre-incubated with the drug-DIG for one hour. The results are shown in the following Table 1.

TABLE 1

Results of the ELISA for detection of anti-IL-6R-antibody antibodies

|  | drug antibody unspecific, oligomeric response | drug antibody unspecific response | drug antibody unspecific, oligomeric response | drug antibody specific, monomeric response | drug antibody specific, monomeric response | drug antibody unspecific, monomeric response |
|---|---|---|---|---|---|---|
| unspiked sample | + | + | + | + | + | + |
| recovered signal in spiked samples | [%] | [%] | [%] | [%] | [%] | [%] |

TABLE 1-continued

Results of the ELISA for detection of anti-IL-6R-antibody antibodies

| | drug antibody unspecific, oligomeric response | drug antibody unspecific response | drug antibody unspecific, oligomeric response | drug antibody specific, monomeric response | drug antibody specific, monomeric response | drug antibody unspecific, monomeric response |
|---|---|---|---|---|---|---|
| ii) anti-IL-6R antibody in monomeric form | 96.5 + | 95.1 + | 93.2 + | 27.9 − | 2.88 − | 63.3 − |
| iii) anti-IL-6R antibody in oligomeric form | 41.1 − | 92.0 + | 12.2 − | 15.3 − | BLQ − | 12.1 − |
| iv) human IgG antibody in monomeric form | 91.9 + | 103.9 + | 88.9 + | 90.8 + | 107.0 + | 73.0 − |
| v) human IgG antibody in oligomeric form | 41.9 − | 98.3 + | 14.9 − | 93.7 + | 100.0 + | 22.5 − |

BLQ = below limit of quantification

Example 10

ELISA for Detection of Anti-IGF-1R Antibody Antibodies

The assay has been performed according to Example 8. The results are shown in the following Table 2.

TABLE 2

Results of the ELISA for detection of anti-IGF-1R-antibody antibodies

| | drug antibody unspecific response | drug antibody specific, oligomeric response (IgM) | drug antibody specific, monomeric response (IgG) |
|---|---|---|---|
| unspiked sample recovered signal in spiked samples | + [%] | + [%] | + [%] |
| ii) anti-IGF-1R antibody in monomeric form | 91.4 + | 89.5 + | 0.90 − |
| iii) anti-IGF-1R antibody in oligomeric form | 82.7 + | 62.4 − | 0.32 − |
| iv) human IgG antibody in monomeric form | 109.1 + | 94.4 + | 95.2 + |
| v) human IgG antibody in oligomeric form | 111.2 + | 96.1 + | 97.4 + |

Example 11

ECLIA for Detection of Anti-IL-13R-Antibody Antibodies

The assay has been performed according to Example 8. Exception: this is an assay using electro-chemiluminescence as detection method. This means that a ruthenium-labeled drug antibody was used as Tracer-DIG instead of digoxygenylated drug antibody and peroxidase-conjugated anti-DIG antibody. The results are shown in the following Table 3.

TABLE 3

Results of the ECLIA for detection of anti-IL-13R-antibody antibodies

| | drug antibody unspecific, monomeric response | drug antibody unspecific, monomeric response | drug antibody specific, monomeric response |
|---|---|---|---|
| unspiked sample signal recovery | + [%] | + [%] | + [%] |
| b-ii) anti-IL-13Ra1 antibody in monomeric form | 3.96 − | 10.87 − | 0.08 − |
| b-iii) anti-IL-13Ra1 antibody in oligomeric form | BLQ − | BLQ − | 0.20 − |
| b-iv) human IgG antibody in monomeric form | BLQ − | 0.61 − | 90.84 + |
| b-v) human IgG antibody in oligomeric form | BLQ − | BLQ − | 85.35 + |

BLQ = below limit of quantification.

The invention claimed is:

1. A method for determining whether an antibody present in a sample is a specific anti-drug antibody or a not-specific anti-drug antibody with an immunoassay, said method comprising:
   a) providing
      a-i) a capture drug antibody, which is said drug antibody conjugated to a solid phase,
      a-ii) a tracer drug antibody, which is said drug antibody conjugated to a detectable label,
   b) contacting said capture drug antibody separately with
      b-i) said sample,
      b-ii) said sample, to which said drug antibody in monomeric form has been added
      b-iii) said sample, to which said drug antibody in oligomeric form has been added,
      b-iv) said sample, to which human immunoglobulin G in monomeric form has been added,
      b-v) said sample, to which human immunoglobulin G in oligomeric form has been added, c) determining an antibody present in said sample to be a specific anti-drug antibody by a positive immunoassay in b-i) and b-iv) and b-v) and a negative immunoassay in b-ii) and b-iii), or determining an antibody present in said sample to be a not-specific anti-drug antibody by a positive immunoassay in b-i) and b-ii) and b-iv) and a negative immunoassay in b-iii) and b-v).

2. A method for distinguishing in a sample an anti-drug antibody to a humanized anti-inflammatory drug antibody from an anti-human IgG antibody with an immunoassay, wherein the method comprises the following steps:

a) providing
- a-i) a capture drug antibody, which is said drug antibody conjugated to a solid phase,
- a-ii) a tracer drug antibody, which is said drug antibody conjugated to a detectable label, b) contacting said capture drug antibody separately with
- b-i) said sample,
- b-ii) said sample, to which said drug antibody in monomeric form has been added,
- b-iii) said sample, to which said drug antibody in oligomeric form has been added,
- b-iv) said sample, to which human immunoglobulin G in monomeric form has been added,
- b-v) said sample, to which human immunoglobulin G in oligomeric form has been added, c) determining an anti-drug antibody to a humanized anti-inflammatory drug antibody by a positive immunoassay in b-i) and b-iv) and b-v) and a negative immunoassay in b-ii) and b-iii), or determining an antibody present in said sample to be an anti-human IgG antibody by a positive immunoassay in b-i) and b-ii) and b-iv) and a negative immunoassay in b-iii) and b-v).

3. The method of claim 1, wherein the capture drug antibody is conjugated to biotin and conjugation to the solid phase is performed via immobilized Avidin or Streptavidin.

4. A kit for determining an anti-drug antibody to a drug antibody in a sample comprising:
a) a streptavidin coated micro titer plate,
b) a reagent for conjugation of a drug antibody to biotin,
c) a reagent for conjugation of said drug antibody to digoxigenin,
d) a horseradish peroxidase conjugated anti-digoxigenin antibody,
e) a reagent for oligomerization of said drug antibody,
f) human immunoglobulin G in monomeric form and
g) human immunoglobulin G in oligomeric form

* * * * *